(12) United States Patent
Duchamp et al.

(10) Patent No.: US 7,951,259 B2
(45) Date of Patent: May 31, 2011

(54) BALLOON CATHETER HAVING A FLEXIBLE DISTAL END

(75) Inventors: Jacky G. Duchamp, Campbell, CA (US); Misty Lynn Gervais, San Marcos, CA (US); Teresita Baerga, San Jose, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 831 days.

(21) Appl. No.: 11/585,488

(22) Filed: Oct. 24, 2006

(65) Prior Publication Data

US 2007/0066989 A1 Mar. 22, 2007

Related U.S. Application Data

(62) Division of application No. 10/318,577, filed on Dec. 12, 2002, now Pat. No. 7,141,059.

(51) Int. Cl.
*A61M 29/00* (2006.01)

(52) U.S. Cl. .................. 156/294; 456/293; 604/96.01

(58) Field of Classification Search .............. 156/293, 156/294; 604/96.01
See application file for complete search history.

(56) References Cited

U.S. PATENT DOCUMENTS

| 3,890,976 | A | | 6/1975 | Bazell et al. |
| 4,894,051 | A | | 1/1990 | Shiber |
| 4,921,483 | A | | 5/1990 | Wijay et al. |
| 4,990,138 | A | | 2/1991 | Bacich et al. |
| 5,057,083 | A | | 10/1991 | Gellman |
| 5,395,330 | A | | 3/1995 | Marcadis et al. |
| 5,643,209 | A | | 7/1997 | Furgoso et al. |
| 5,653,690 | A | | 8/1997 | Booth et al. |
| 6,139,525 | A | * | 10/2000 | Davis-Lemessy et al. ... 604/103 |
| 6,165,152 | A | | 12/2000 | Becker et al. |
| 6,206,852 | B1 | | 3/2001 | Lee |
| 6,258,108 | B1 | | 7/2001 | Lary |
| 6,364,894 | B1 | * | 4/2002 | Healy et al. .................. 606/194 |
| 6,368,301 | B1 | | 4/2002 | Hamilton et al. |
| 6,596,217 | B1 | * | 7/2003 | Davis-Lemessy et al. ... 264/400 |

FOREIGN PATENT DOCUMENTS

| EP | 1 103 280 A1 | 5/2001 |
| JP | 7231941 A | 9/1995 |

* cited by examiner

*Primary Examiner* — Jeff H Aftergut
*Assistant Examiner* — Jaeyun Lee
(74) *Attorney, Agent, or Firm* — Fulwider Patton LLP; Thomas H. Majcher, Esq.

(57) ABSTRACT

A catheter having an elongated shaft with a proximal end, a distal end, and at least one lumen, and a distal portion of the shaft being at least in part within an outer sheath having a wedge-shaped distal end. In one embodiment, the outer sheath around the distal end of the shaft is the distal skirt section of the balloon. In an alternative embodiment, the outer sheath is a sleeve member having at least a portion located distal to the distal end of the balloon.

12 Claims, 3 Drawing Sheets

BALLOON CATHETER HAVING A FLEXIBLE DISTAL END

This application is a division of U.S. patent application Ser. No. 10/318,577, filed Dec. 12, 2002, now U.S. Pat. No. 7,141,059 issued Nov. 28, 2006.

BACKGROUND OF THE INVENTION

This invention generally relates to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

An essential step in effectively performing a PTCA procedure is properly positioning the balloon catheter at a desired location within the coronary artery. To properly position the balloon at the stenosed region, the catheter shaft must be able to transmit force along the length of the catheter shaft to allow it to be pushed through the vasculature. However, the catheter shaft must also retain sufficient flexibility to allow it to track over a guidewire through the often tortuous vasculature. Additionally, the catheter also must have good crossability (i.e., the ability of the catheter distal end to cross stenosed portions of the vascular anatomy).

Conventional intravascular catheters have commonly included a soft distal tip to prevent or minimize injury to the vessel during advancement of the catheter therein. One difficulty has been forming a connection between the soft tip and the catheter which is sufficiently strong to prevent disengagement of the soft tip or kinking at the junction between the soft tip and catheter shaft. Additionally, it is necessary to balance the strength of the connection between the soft tip and the catheter shaft with the need to minimize the stiffness of the distal end of the catheter. Minimizing the stiffness of the distal end of the catheter results in improved maneuverability of the catheter.

Accordingly, it would be a significant advance to provide a catheter with a soft tip having improved performance. This invention satisfies these and other needs.

SUMMARY OF THE INVENTION

The invention is directed to a catheter having an elongated shaft with a proximal end, a distal end, and at least one lumen, and a distal portion of the shaft being at least in part within an outer sheath having a wedge-shaped distal end.

In a presently preferred embodiment, the catheter is a balloon catheter with a balloon on a distal shaft section, having an interior in fluid communication with the at least one lumen of the catheter shaft. A balloon catheter of the invention generally comprises an elongated shaft having a proximal shaft section, a distal shaft section, an inflation lumen extending within the proximal and distal shaft sections, and a guidewire receiving lumen extending at least within the distal shaft section, and an inflatable balloon on the distal shaft section with an interior in fluid communication with the inflation lumen. The balloon typically has a proximal skirt section and a distal skirt section sealingly secured to the shaft, and an inflatable section therebetween. In a presently preferred embodiment, the shaft comprises an outer tubular member defining the inflation lumen, and an inner tubular member defining at least a portion of the guidewire receiving lumen. However, a variety of suitable shaft designs may be used including dual-lumen type shafts. The balloon catheter of the invention may comprise a variety of suitable balloon catheters, including coronary and peripheral dilatation catheters, stent delivery catheters, drug delivery catheters, and the like.

In one embodiment, the distal skirt section of the balloon forms the wedge-shaped outer sheath around the distal end of the shaft. In an alternative embodiment, the outer sheath is a sleeve member having at least a portion located distal to the distal end of the balloon. The wedge-shaped distal end has an angled (i.e., truncated) end formed by a distal leading face which is oriented at an angle of about 30 to about 60 degrees, more preferably about 45 to about 55 degrees relative to the longitudinal axis of the shaft. The wedge-shaped end of the outer sheath provides distally increasing flexibility for a smooth transition in stiffness along the distal end of the catheter, to improve handling and performance and minimize kinking. In a presently preferred embodiment, the outer sheath has a proximal cylindrical section proximal to the wedge-shaped distal end. The proximal section of the outer sheath preferably has a circular or oblong transverse cross sectional shape, although it can have a variety of suitable shapes.

In a presently preferred embodiment, a distal tip member having at least a portion distal to the inner tubular member forms the distal end of the shaft, and defines a distal portion of the guidewire lumen in fluid communication with the portion of the guidewire lumen defined by the inner tubular member. The distal tip member provides improved flexibility at the shaft distal end for improved maneuverability. However, in an alternative embodiment, the distal tip member is omitted, and the distal end of the inner tubular member defines the distal end of the shaft. The distal tip member is typically softer and more flexible than the inner tubular member. In one embodiment, the distal tip member is formed of a material having a lower Shore Durometer hardness than a polymeric material forming at least part of the inner tubular member, to provide a soft, flexible, atraumatic distal end, which consequently provides improved catheter maneuverability and decreases the risk of damage to the patient's vessel during advancement of the catheter therein. The Shore Durometer hardness of the polymeric material forming the tip member is typically about 40 D to about 70 D, preferably about 55 D to about 65 D. In a presently preferred embodiment, the distal tip member is formed of a polyurethane, including a polyurethane copolymer such as PELLETHANE (a polyester polyurethane copolymer), available from Dow Plastics. However, the distal tip member may be formed of a variety of suitable materials, including polyolefin based copolymers such as a polyethylene based adhesive polymers such as an ethylene-acrylic acid copolymer which is sold commercially as PRIMACOR by Dow Chemical Co., and polyether block amide polymer such as PEBAX (available from Autochem).

In a presently preferred embodiment, the wedge-shaped outer sheath is around a distal end of the inner tubular member and at least a proximal end of the distal tip member. However, a variety of suitable configurations may be used in which the location of the distal end of the shaft relative to the outer sheath varies. For example, in one embodiment, the distal end of the shaft is distal to the distal end of the wedge-shaped outer sheath, to provide an atraumatic leading distal end. However, in an alternative embodiment, the distal end of the wedge-shaped outer sleeve is distal to the distal end of the shaft, to provide enhanced support at the distal tip for improved tensile strength and a decrease in the distance between the distal end of the catheter and the proximal end of the balloon skirt section. In the embodiment having a distal tip member distal to the inner tubular member, the distal end of the inner tubular member is preferably located proximal to the wedge-shaped distal end of the outer sheath (i.e., proximal to the proximal end of the distal leading face of the wedge-shaped distal end of the outer sheath), although it may alternatively be located distal to the proximal end of the wedge-shaped distal end of the outer sheath, or proximal or distal to the outer sheath, depending on the desired performance characteristics of the catheter.

The outer sheath has at least a section secured to the inner tubular member and/or the distal tip member. In the embodiment in which the outer sheath is the distal skirt section of the balloon, at least a section of the balloon distal skirt section is bonded, for example by fusion or adhesive bonding, to the shaft. In a presently preferred embodiment, the proximalmost portion of the distal skirt section of the balloon is typically not bonded to the inner tubular member or distal tip therein. The section of the outer sheath bonded to the underlying section of the shaft typically flows and fuses together with the polymeric material forming at least an outer surface of the underlying section of the shaft (i.e., the inner tubular member and/or distal tip), so that the bonded outer surface of the outer sheath typically has a distally tapering outer diameter.

The catheter of the invention has excellent maneuverability and crossability due to the distal end of the catheter having a wedge-shaped outer sheath around the distal end of the shaft. The wedge-shaped outer sheath provides gradually decreasing flexibility at the catheter distal end, for improved handling and performance. Moreover, in the embodiment having a soft distal tip forming the distal end of the shaft, the catheter has excellent tensile strength at the distal tip attachment, without disadvantageously increasing the stiffness or profile of the distal end of the catheter. These and other advantages of the invention will become more apparent from the wing detailed description and exemplary drawings.

DETAILED DESCRIPTION OF THE INVENTION

Figure 1:
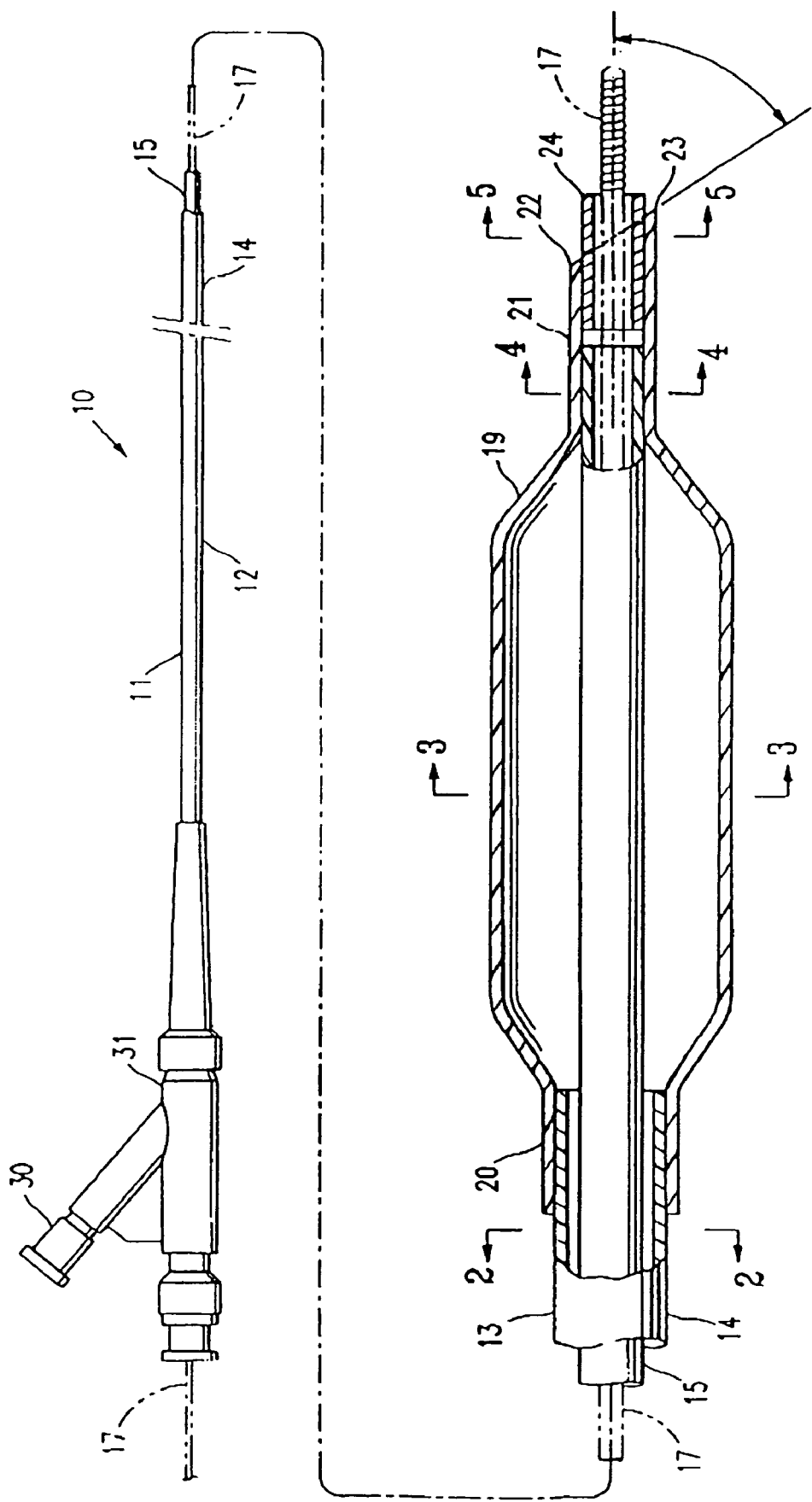
FIG. 1 is an elevational view, partially in section, of a balloon catheter which embodies features of the invention.
Figure 3:
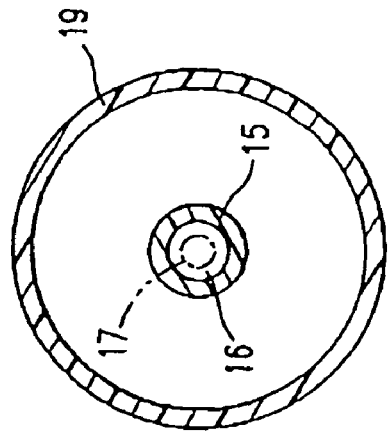
FIG. 3 is a transverse cross sectional view of the catheter shown in FIG. 1, taken along line 3-3.
Figure 2:
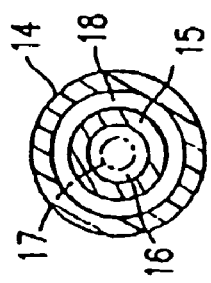
FIG. 2 is a transverse cross sectional view of the catheter shown in FIG. 1, taken along line 2-2.

FIG. 1 illustrates an over-the-wire balloon catheter 10 embodying features of the invention. Catheter 10 generally comprises an elongated catheter shaft 11 having a proximal end, a distal end, a proximal shaft section 12, a distal shaft section 13, an outer tubular member 14, and an inner tubular member 15. Inner tubular member 15 defines a guidewire lumen 16 adapted to slidingly receive a guidewire 17, and the coaxial relationship between outer tubular member 14 and inner tubular member 15 defines annular inflation lumen 18, as best shown in FIG. 2, illustrating a transverse cross section of the catheter of FIG. 1, taken along line 2-2. An inflatable balloon 19 is disposed on the distal shaft section 13, having a proximal skirt section 20 sealingly secured to the distal end of outer tubular member 14, and a distal skirt section 21 sealingly secured to the distal end of inner tubular member 15, so that its interior is in fluid communication with inflation lumen 18. An adapter 31 at the proximal end of the shaft is configured to provide access to guidewire lumen 16, and to direct inflation fluid through arm 30 into inflation lumen 18. FIG. 1 illustrates the balloon 19 inflated. The distal end of catheter may be advanced to a desired region of a patient's body lumen in a conventional manner, and balloon 19 inflated to perform a procedure, and the balloon deflated, and the catheter repositioned or withdrawn from the body lumen. FIG. 3 illustrates a transverse cross section of the catheter of FIG. 1, taken along line 3-3.

Figure 5:
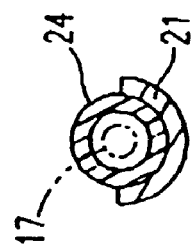
FIG. 5 is a transverse cross sectional view of the catheter shown in FIG. 1, taken along line 5-5.
Figure 4:
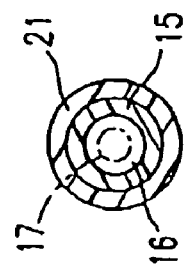
FIG. 4 is a transverse cross sectional view of the catheter shown in FIG. 1, taken along line 4-4.

The catheter 10 has a wedge-shaped outer sheath, which in the embodiment of FIG. 1 is the distal skirt section 21 of the balloon. The tapered distal leading face or edge forming the wedge-shape of the distal skirt section 21 tapers at an angle relative to the longitudinal axis of the shaft. In the embodiment of FIG. 1, the angle is about 55 degrees relative to the longitudinal axis of the shaft, although alternative angles can be used depending on the materials forming the distal end of the catheter and the desired performance of the catheter. FIGS. 4 and 5 illustrate transverse cross sections of the catheter of FIG. 1, taken along lines 4-4, and 5-5, respectively.

Although illustrated with a circular transverse cross sectional shape in the figures, the distal skirt section 21 and underlying shaft section can have a variety of suitable shapes including oblong, and the like. The balloon distal skirt section 21 has a proximal section which is continuous around the shaft therein, as best illustrated in FIG. 4. In contrast, at the wedge-shaped distal leading face, the balloon distal skirt section 21 extends only partially around the shaft therein, as best illustrated in FIG. 5.

The distal leading face of the wedge-shaped distal skirt section 21 has a proximal end 22 and a distal end 23 and a length extending from the proximal end 22 to the distal end 23 thereof. The distal skirt section 21 has a cylindrical section proximal to the wedge-shaped distal leading face. Preferably, the length of the wedge-shaped distal leading face is about 20 to about 75% of the length of the distal skirt section 21, and in one embodiment is about 2.5 to about 4 mm.

In the embodiment of FIG. 1, the distal end of the shaft is located distal to the distal end of the wedge-shaped distal skirt section 21. A distal tip member 24 forms the distal end of the shaft. In the embodiment of FIG. 1, the wedge-shaped distal skirt section 21 surrounds a distal end of the inner tubular member 15 and a proximal end of the distal tip member 24. The distal tip member 24 defines a distal portion of the guidewire lumen 16 in fluid communication with the portion of the guidewire lumen 16 defined by the inner tubular member 15. In the embodiment of FIG. 1, the distal tip member 24 extends from a location proximal of the proximal end 22 of the wedge shaped distal leading face, to a location distal of the distal end 23 of the wedge shaped distal leading face, so that the distal tip member 24 extends through the angled end of the wedge-shaped distal skirt section 21.

In the embodiment of FIG. 1, the distal tip member 24 has a proximal end spaced distally apart from the inner tubular member 15, forming a gap therebetween which is surrounded by the cylindrical proximal portion of the balloon distal skirt section 21. Although illustrated with a gap between the inner tubular member 15 and the distal tip member 24, a variety of suitable junctions between the distal tip member and the inner tubular member may be used including lap and butt joints. Additionally, in an alternative embodiment, tip member 24 is omitted, so that the inner tubular member 15 would extend in place of the tip member 24 through the angled end of the wedge-shaped distal skirt section 21.

The wedge-shaped distal skirt section 21 of the balloon 19 is bonded, and preferably fusion bonded, to the shaft inner tubular member 15 and distal tip member 24. In a method of making a balloon catheter of the invention, the wedge-shape is formed at the distal end of the distal skirt section 21 of the balloon 19 preferably by mechanically cutting a cylindrical end of the skirt section, although it may alternatively be formed by a variety of suitable methods including other methods of material removal such as laser cutting. Prior to being bonded to the catheter shaft, the balloon distal skirt section 21 is a tubular member with the wedge-shaped distal end having a lumen therein configured to receive the catheter shaft therein and the wedge-shaped distal leading face defines a tapering port in the distal end of the balloon distal skirt section 21, so that the distal skirt section can be placed in surrounding relation to the shaft and subsequently bonded thereto. In a presently preferred embodiment, the bond extends from a location distal to the proximal end of the distal skirt section 21 to the distal end of the distal skirt section 21 (i.e., to the distal end 23 of the wedge-shaped distal leading face in the embodiment of FIG. 1). Thus, in one embodiment, a proximal part of the distal skirt section 21 is not bonded to the inner tubular member 15.

Figure 6:
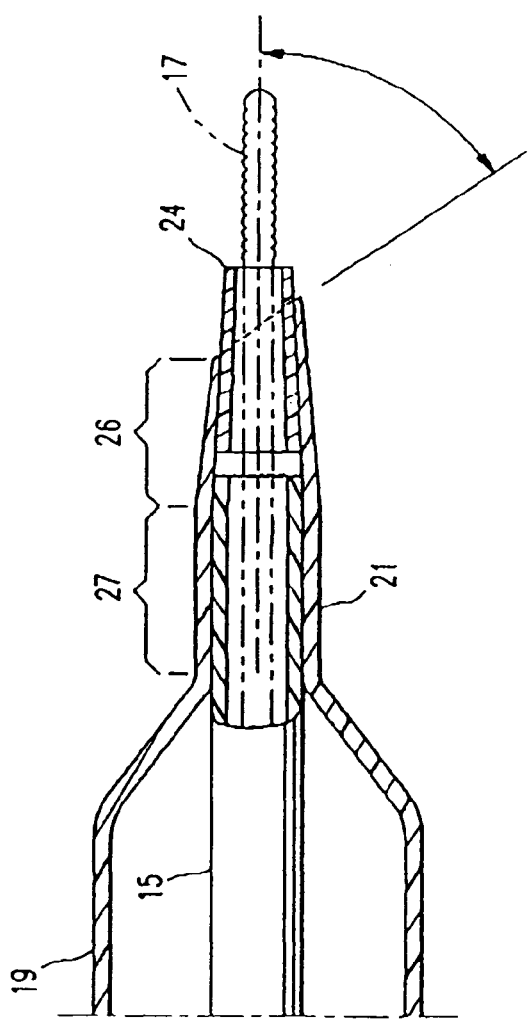
FIG. 6 is an enlarged, longitudinal cross sectional view of an alternative embodiment of the catheter of FIG. 1, having a balloon distal skirt section with a tapering outer surface.

Although illustrated in FIG. 1 with sharp straight edges for ease of illustration, it should be understood that during bonding of the balloon distal skirt section 21 to the distal end of the shaft, the polymeric materials typically melt or soften, and flow. As a result, the outer surface of the balloon distal skirt section 21 typically tapers distally to a smaller outer diameter along the length of the bond. For example, in a presently preferred embodiment, a mandrel is placed in the inner lumen of the shaft, and a heat shrink sleeve is provided on the outer surface of the wedge-shaped distal skirt section 21. Heat is applied to a distal length thereof to bond the sheath and tip together, causing the polymeric materials of the outer sheath and distal tip to flow distally as the members are forced down onto the mandrel. Therefore, although illustrated in FIG. 1 with straight outer surfaces parallel to the longitudinal axis of the shaft and sharply terminating ends, it should be understood that the outer surface of the wedge-shaped distal skirt section 21 and distal tip 24 typically taper distally along the heated/bonded lengths thereof to a smaller outer diameter. FIG. 1 therefore illustrates the balloon catheter either prior to heat fusion bonding the distal skirt section 21 of the balloon to the inner tubular member 15 and distal tip member 24 in which the polymeric materials are caused to flow distally during fusion bonding, or with the distal skirt section 21 adhesively bonded to the inner tubular member 15 and distal tip member 24 so that the polymeric materials are not caused to flow distally during bonding. FIG. 6 illustrates an embodiment having the outer surface of the wedge-shaped distal skirt section 21 and distal tip 24 tapering distally along the heated/bonded lengths thereof. The fusion bonded portion 26 of the distal skirt section 21 has a tapered outer and inner surface forming a distally decreasing wall thickness. A non-bonded portion 27 is proximal to the bonded portion 26 and is not bonded to the underlying section of the inner tubular member 15. The length of bonded portion 26 is typically about 60 to about 80% of the length of the balloon distal skirt section 21.

Preferably, the wedge-shape of the distal leading face of the distal skirt section 21 is still present after bonding, albeit with a smoother, more gradual transition from the distal skirt section 21 to the distal tip 24 due to the tapering outer surfaces. In a presently preferred embodiment, the angle of the wedge-shaped distal leading face of the distal skirt section 21 does not change as a result of the fusion bonding process.

Figure 7:
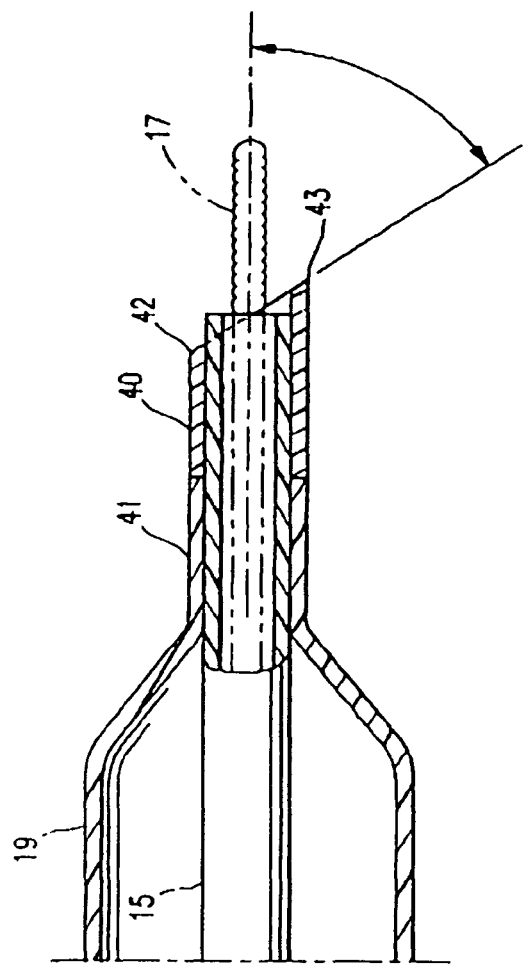
FIG. 7 is an enlarged, longitudinal cross sectional view of an alternate embodiment of a catheter embodying features of the invention, having a wedge-shaped sleeve member around the distal end of the shaft.

FIG. 7 illustrates a longitudinal cross section of an alternative embodiment, in which the wedge-shaped outer sheath of balloon catheter 10 is a wedge-shaped outer sleeve member 40 (instead of the wedge-shaped balloon distal skirt section 21 of the embodiment of FIG. 1). In the embodiment of FIG. 7, the balloon 19 has a cylindrical distal skirt section 41 with a squared-off distal leading face abutting the proximal end of the wedge-shaped outer sleeve member 40. Similar to the embodiment of FIG. 1, the wedge-shaped outer sleeve member 40 has a tapered distal leading face forming the wedge-shape of the outer sleeve member 40 which tapers at an angle relative to the longitudinal axis of the shaft.

In the embodiment of FIG. 7, the distal end of the shaft is located proximal to the distal end of the wedge-shaped outer sleeve member 40. The soft tip member 24 of the embodiment of FIG. 1 is omitted, so that inner tubular member 15 forms the distal end of the shaft. In the embodiment of the FIG. 7, the distal end of the inner tubular member 15 extends from a location proximal of the proximal end 42 of the wedge-shaped distal leading face, to a location proximal of the distal end 43 of the wedge-shaped distal leading face (i.e., the distal end of the inner tubular member 15 is located between the proximal and distal ends 42, 43 of the wedge-shaped distal leading face of the outer sleeve member 40), so that only part of the distal end of the inner tubular member extends through the angled end of the wedge-shaped outer sleeve member 40. With the distal end of the inner tubular member located between the proximal and distal ends 42, 43 of the wedge-shaped distal leading face, the distal end of the inner tubular member 15 is supported by the outer sleeve member 40 but is only partially surrounded by it. However, as discussed above in relation to the embodiment of FIG. 1, the distal end of the wedge-shaped outer sleeve member 40 can be located in a variety of alternative longitudinal positions relative to the distal end of the inner tubular member 15 in alternative embodiments. For example, in one embodiment, the distal end of the inner tubular member 15 is at the distal end 43 of the wedge-shaped outer sleeve member 40 (i.e., the distal end of the inner tubular member 15 is slightly distal to its location in FIG. 7), so that the distal ends are radially aligned.

The outer sleeve member 40 and balloon distal skirt section 41 are secured to the inner tubular member 15 as discussed above in relation to the embodiment of FIG. 1. The outer sleeve member 40 is typically fusion bonded to the inner tubular member 15, although it may alternatively be formed of a heat shrink polymeric material and heat shrunk down onto the inner tubular member 15.

Outer sleeve member 40 typically has a length of about 1 to about 3 mm. The length and angle of the wedge-shaped distal leading face of the outer sleeve member 40 are similar to those of the wedge-shaped distal leading face of the distal skirt section 21 of the embodiment of FIG. 1. Similarly, although illustrated with sharp, non-tapering outer surfaces in FIG. 7, it should be understood that the outer sleeve member 40 and/or balloon distal skirt section 41 will typically have tapering outer surfaces after heat bonding the balloon 19 and sleeve member 40 to the inner tubular member 15, as discussed above in relation to the embodiment of FIG. 1. Additionally, although not illustrated, a distal tip member such as tip member 24 may be provided in the embodiment having a wedge-shaped outer sleeve member 40, as for example with a tip member (not shown) butt-joined to the distal end of the inner tubular member 15 with wedge-shaped outer sleeve member 40 sealingly surrounding the butt joint.

To the extent not previously discussed herein, the various catheter components may be formed and joined by conventional materials and methods. For example, inner tubular member 15 can be formed by conventional techniques, such as by extruding and necking materials found useful in intravascular catheters such a polyethylene, polyvinyl chloride, polyesters, polyamides, polyimides, polyurethanes, and composite materials, and is preferably a multilayered tubular member. Additionally, although not illustrated, coiled or braided reinforcements may be included in the shaft at various locations, as is conventionally known.

The length of the dilatation catheter 10 is generally about 108 to about 200 centimeters, preferably about 137 to about 145 centimeters, and typically about 140 centimeters for PTCA. The outer tubular member 14 distal section has an outer diameter (OD) of about 0.028 to about 0.036 inch (0.70-0.91 mm), and an inner diameter (ID) of about 0.024 to about 0.035 inch (0.60-0.89 mm), and the outer tubular member 14 proximal section has an OD of about 0.017 to about 0.034 inch (0.43-0.87 mm), and an inner diameter (ID) of about 0.012 to about 0.022 inch (0.30-0.56 mm). The inner tubular member 15 has an OD of about 0.017 to about 0.026 inch (0.43-0.66 mm), and an ID of about 0.015 to about 0.018 inch (0.38-0.46 mm) depending on the diameter of the guidewire to be used with the catheter. The balloon 19 has a length of about 8 mm to about 40 mm, and an inflated working diameter of about 1.5 mm to about 5 mm.

While the present invention has been described herein in terms of certain preferred embodiments, those skilled in the art will recognize that modifications and improvements may be made without departing from the scope of the invention. For example, although the catheter 10 illustrated in the Figures is an over-the-wire balloon catheter, the catheter of the invention may be a variety of suitable balloon catheters, including rapid exchange type balloon catheters having a guidewire proximal port located distal to the proximal end of the shaft, a guidewire distal port in the distal end of the shaft, and a relatively short guidewire lumen extending therebetween. While discussed primarily in terms of a wedge-shaped distal skirt section, it should be understood that the balloon may have a wedge-shaped proximal skirt section or sleeve member. While individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A method of making a balloon catheter, comprising:
providing a catheter shaft;
forming a balloon with a distal skirt section, the distal skirt section having a proximal section which is continuous when placed on the catheter shaft and a wedge-shaped distal end forming a wedge-shaped distal leading face, the distal skirt section only extending partially around the catheter shaft at the distal leading face when place on the catheter shaft, the distal skirt section having a lumen configured for receiving a distal section of the catheter shaft therein;
positioning the distal section of the catheter shaft in the distal skirt section lumen;
positioning a mandrel within said catheter shaft; and
bonding at least a portion of the balloon distal skirt section to the shaft distal section, to secure the balloon to the shaft, so that the balloon has an interior in fluid communication with an inflation lumen of the shaft.

2. The method of claim 1 wherein the balloon is formed of a polymeric material and wherein bonding at least a portion of the balloon distal skirt section to the shaft distal section comprises heat fusion bonding the balloon distal skirt section to the shaft distal section by heating the polymeric material forming the portion of the balloon distal skirt section and the shaft distal section therein, so that the heated polymeric material of the balloon distal skirt section flows distally to form a distally tapering outer surface along the length of the fusion bond.

3. The method of claim 1 wherein forming the wedge-shaped distal end comprises mechanically cutting through the distal skirt section at an angle of about 30 to about 60 degrees relative to a longitudinal axis of the distal skirt section.

4. A method of making a balloon catheter, comprising:
a) forming a balloon with a distal skirt section, the distal skirt section having a wedge-shaped distal end and a lumen configured for receiving a distal section of a catheter shaft therein;
b) positioning the distal section of the catheter shaft in the distal skirt section lumen;
c) positioning a mandrel within said catheter shaft; and
d) bonding at least a portion of the balloon distal skirt section to the shaft distal section, to secure the balloon to the shaft, so that the balloon has an interior in fluid communication with an inflation lumen of the shaft, wherein the shaft includes a distal tip member attached to a distal end of the shaft, and the distal section of the shaft is positioned in the distal skirt section lumen such that the distal end of the shaft is located distal to at least part of the wedge-shaped distal end of the distal skirt section.

5. The method of claim 1 wherein the wedge-shaped distal end has an angled distal leading face, and the distal section of the catheter shaft extends distally at least in part out the distal leading face, so that the distal leading face extends partially around the catheter shaft circumference by an amount is greater than 0 degree and less than 360 degrees when viewed in a cross-sectional plane perpendicular to the longitudinal axis of the shaft and which decreases distally toward a distal end of the distal leading face, and the distal end of the catheter shaft is distal to at least part of the distal leading face.

6. The method of claim 1 wherein the catheter shaft includes a distal tip member attached to a distal end of the shaft, and the distal section of the shaft is positioned in the distal skirt section lumen such that the distal end of the shaft is located distal to at least part of the wedge-shaped distal end of the distal skirt section.

7. A method of making a balloon catheter, comprising:
 a) forming a balloon with a distal skirt section, the distal skirt section having a wedge-shaped distal end and a lumen configured for receiving a distal section of a catheter shaft therein;
 b) positioning the distal section of the catheter shaft in the distal skirt section lumen;
 c) positioning a mandrel within said catheter shaft; and
 d) bonding at least a portion of the balloon distal skirt section to the shaft distal section, to secure the balloon to the shaft, so that the balloon has an interior in fluid communication with an inflation lumen of the shaft, wherein the wedge-shaped distal end has an angled distal leading face which lies in a plane that is not perpendicular to the longitudinal axis of the catheter shaft.

8. The method of claim 7 wherein the angled distal leading face has an oval shape.

9. The method of claim 7 wherein the catheter shaft has a distal tip member attached to the distal end of the catheter shaft.

10. The method of claim 7 wherein the wedge-shaped distal leading face is oriented at an angle of about 30 to about 60 degrees relative to the longitudinal axis of the shaft.

11. The method of claim 7 wherein the wedge-shaped distal leading face has a proximal end and a length of about 2.5 to about 4 mm extending from the proximal to the distal end thereof, and the outer sheath has a cylindrical section proximal to the wedge-shaped distal leading face.

12. The method of claim 11 wherein the length of the wedge-shaped distal leading face is about 20 to about 75% of the length of the outer sheath.

\* \* \* \* \*